US011123368B2

(12) United States Patent
Terness et al.

(10) Patent No.: US 11,123,368 B2
(45) Date of Patent: Sep. 21, 2021

(54) IMMUNOSUPPRESSIVE BLOOD CELLS AND METHODS OF PRODUCING THE SAME

(71) Applicant: Universitatsklinikum Heidelberg, Heidelberg (DE)

(72) Inventors: Peter Terness, Eppelheim (DE); Gerhard Opelz, Heidelberg (DE); Helmut Simon, Dielheim (DE); Sandra Ehser, Mauer (DE); Christian Kleist, Neckargemund (DE); Flavius Sandra-Petrescu, Karlsruhe (DE); Mircea Iancu, Mannheim (DE); Lucian Jiga, Oldenburg (DE); Jing-Jing Chuang, Tainan (TW); Thilo Oelert, Heidelberg (DE)

(73) Assignee: Universitatsklinikum Heidelberg, Heidelberg (DE)

( * ) Notice: Subject to any disclaimer, the term of this patent is extended or adjusted under 35 U.S.C. 154(b) by 0 days.

(21) Appl. No.: 15/600,268

(22) Filed: May 19, 2017

(65) Prior Publication Data

US 2017/0319619 A1    Nov. 9, 2017

Related U.S. Application Data

(62) Division of application No. 14/536,456, filed on Nov. 7, 2014, which is a division of application No. 13/001,729, filed as application No. PCT/EP2009/058169 on Jun. 30, 2009, now abandoned.

(30) Foreign Application Priority Data

Jun. 30, 2008 (EP) .................................... 08011780

(51) Int. Cl.
*C12N 5/078* (2010.01)
*A61K 39/00* (2006.01)
*A61K 35/14* (2015.01)
*A61K 31/164* (2006.01)
*A61K 31/407* (2006.01)
*A61K 31/5377* (2006.01)
*A61K 31/7072* (2006.01)
*A61K 38/16* (2006.01)
*A61K 38/17* (2006.01)
*A61K 35/12* (2015.01)

(52) U.S. Cl.
CPC ............ *A61K 35/14* (2013.01); *A61K 31/164* (2013.01); *A61K 31/407* (2013.01); *A61K 31/5377* (2013.01); *A61K 31/7072* (2013.01); *A61K 38/16* (2013.01); *A61K 38/1709* (2013.01); *A61K 39/00* (2013.01); *A61K 39/0008* (2013.01); *C12N 5/0634* (2013.01); *A61K 2035/122* (2013.01); *C12N 2501/06* (2013.01)

(58) Field of Classification Search
None
See application file for complete search history.

(56) References Cited

U.S. PATENT DOCUMENTS

| 6,699,466 | B1 | 3/2004 | Center et al. |
| 7,132,243 | B2 | 11/2006 | Matsushita et al. |
| 7,658,926 | B2 | 2/2010 | Zang et al. |
| 2003/0149011 | A1 | 8/2003 | Ackerman et al. |
| 2007/0218066 | A1 | 9/2007 | Das et al. |
| 2010/0074904 | A1* | 3/2010 | Schneider ............ G01N 33/505 424/152.1 |

FOREIGN PATENT DOCUMENTS

| EP | 1 739 166 A1 | 1/2007 |
| WO | WO 99/13904 | 3/1999 |
| WO | WO 99/50394 | 10/1999 |
| WO | WO 2004/044149 A2 | 5/2004 |

OTHER PUBLICATIONS

Terness et al ( Human Immunol, 2009, v.70 pp. 506-512).*
Jiga et al (Transplantation, 2007, v.83, pp. 347-350 ).*
Wang et al Transplantation, 2006,v.82.pp. 1537-1540.*
Terness et al, 2009, v.70 pp. 506-512.*
Final Office Action issued in related U.S. Appl. No. 14/536,456, dated Oct. 25, 2017.
Bakri et al., "Balance of MafB and PU.1 specifies alternative macrophage or dendritic cell fate," *Blood*, vol. 105, No. 7, pp. 2707-2716 (2005).
Bar-Or et al., "Induction of Antigen-Specific Tolerance in Multiple Sclerosis After Immunization with DNA Encoding Myelin Basic Protein in a Randomized, Placebo-Controlled Phase ½ Trial," *Arch. Neurol.*, vol. 64, No. 10, pp. 1407-1415 (2007).
Bar-Or et al., Antigen-specific immunomodulation in MS patients treated with MBP encoding DNA plasmid (BHT-3009) alone or combined with atorvastatin, *Multiple Sclerosis*, S167, p. 632, 2 pgs., (2011).
Bielekova et al., "Encephalitogenic potential of the myelin basic protein peptide (amino acids 83-99) in multiple sclerosis: Results of a phase II clinical trial with an altered peptide ligand," *Nature Medicine*, vol. 6, No. 10, pp. 1167-1175 (2000).
Blattman et al., "Estimating the Precursor Frequency of Naïve Antigen-specific CD8 T Cells," *J. Exp. Med.*, vol. 195, No. 5, pp. 657-664 (2002).
Chang et al., Tolerization of dentritic cells by Ts cells: the crucial role of inhibitory receptors ILT3 and ILT4, *Nature Immun.*, vol. 3, No. 3, pp. 237-243 (2002).
Cohen et al., "GILZ expression in human dendritic cells redirects their maturation and prevents antigen-specific T lymphocyte response," *Blood*, vol. 107, No. 5, pp. 2037-2044 (2006).
Collins et al., "A small interfering RNA screen for modulators of tumor cell motility identifies MAP4K4 as a promigratory kinase," *PNAS*, vol. 103, No. 10, pp. 3775-3780 (2006).

(Continued)

*Primary Examiner* — Michail A Belyavskyi
(74) *Attorney, Agent, or Firm* — Foley & Lardner LLP

(57) ABSTRACT

The present invention refers to a method of producing immunosuppressive bleed cells that can be used for the treatment of autoimmune diseases, in particular multiple sclerosis, organ graft rejection and graft-versus-host disease.

18 Claims, 9 Drawing Sheets

(56) References Cited

OTHER PUBLICATIONS

Crosier et al., "A functional isoform of the human granulocyte/macrophage colony-stimulating factor receptor has an unusual cytoplasmic domain," *Proc. Natl. Acad. Sci.*, vol. 88, pp. 7744-7748 (1991).

Fridkis-Hareli et al., "Novel synthetic amino acid copolymers that inhibit autoantigen-specific T cell responses and suppress experimental autoimmune encephalomyelitis," *The Journ. of Clin. Investigation*, vol. 109, No. 12, pp. 1635-1643 (2002).

Harty et al., "Shaping and reshaping CD8+ T-cell Memory," *Nature Reviews*, vol. 8, pp. 107-119 (2008).

Hemmer et al., "New Concepts in the Immunopathogenesis of Multiple Sclerosis," *Neuroscience*, vol. 3, pp. 291-301 (2002).

Hirata et al., "Prevention of Experimental Autoimmune Encephalomyelitis by Transfer of Embryonic Stem Cell-Derived Dendritic Cells Expressing Myelin Oligodendrocyte Glycoprotein Peptide along with Trail or Programmed Death-1 Ligand," *The Journ. of Immun.*, pp. 1888-1897 (2005).

Ho et al., "A Suppressive Oligodeoxynucleotide Enhances the Efficacy of Myelin Cocktail/IL-4-Tolerizing DNA Vaccination and Terats Autoimimmune Disease," *The Journ. of Immunology*, pp. 6226-6234 (2005).

Huang et al., "Autoantigen-pulsed dendritic cells induce tolerance to experimental allergic encephalomyelitis (EAE) in Lewis rats," *Clin. Exp. Immunol.*, vol. 122, pp. 437-444 (2000).

Hugues et al., "Distinct T cell dynamics in lymph nodes during the induction of tolerance and immunity," *Nature Immunology*, vol. 5, No. 12, pp. 1235-1242 (2004).

Iruretagoyena et al., "Inhibition of Nuclear Factor kB Enahnces the Capacity of Immature Dendritic Cells to Induce Antigen-Specific Tolerance in Experimental Autoimmune Encephalomyelitis," *The Journ. of Pharm. and Exper. Therapeutics*, vol. 318, No. 1, pp. 59-67 (2006).

Jiga et al., "Inhibition of Heart Allograft Rejection with Mitomycin C-Treated Donor Dendritic Cells," *Transplantation*, vol. 83, No. 3, pp. 347-350 (2007).

Johnson et al., "Copolymer 1 reduces relapse rate and improves disability in relapsing-remitting multiple sclerosis: Results of phase III multicenter, double-blind, placebo-controlled trial," *Neurology*, pp. 1268-1276 (1995).

Kamphuis et al., "Heat-shock protein 60 as a toll for novel therapeutic strategies that target the induction of regulatory T cells in human arthritis," *Expert Opin. Biol. Therapy*, pp. 579-589 (2006).

Kappos et al., "Induction of a non-encephalitogenic type 2 T helper-cell autoimmune response in multiple sclerosis after administration of an altered peptide ligand in a placebo-controlled, randomized phase II trial," *Nature Medicine*, vol. 6, No. 10, pp. 1176-1182 (2000).

Li et al., "Dendritic Cells Transduced with SOCS-3 Exhibit a Tolerogenic/DC2 Phenotype That Directs Type 2 Th Cell Differentiation In Vitro and In Vivo," *The Journ. of Immun.*, pp. 1679-1688 (2006).

Liu et al., "Immune Tolerance After Delivery of Dying Cells to Dentritic Cells in Situ," *J. Exp. Med.*, vol. 196, No. 8, pp. 1091-1097 (2002).

Liu et al., "Three distinct signaling responses by murine fibroblasts to genotixic stress," *Nature*, vol. 384, pp. 273-276 (1996).

Lo et al., "Dendritic cell subsets and type I diabetes: Focus upon DC-based therapy," *Autoimmunity Reviews*, vol. 5, pp. 419-423 (2006).

Lutz et al., "An advanced culture method for generating large quantities of highly pure dendritic cells from mouse bone marrow," *Journ. of Immun.*, vol. 223, pp. 77-92 (1999).

Menges et al., "Repetitive Injections of Dendritic Cells Matured with Tumor Necrosis Factor α Induce Antigen-specific Protection of Mice from Autoimmunity," *J. Exp. Med.*, pp. 15-21 (2002).

Muller et al., "Interleukin-10-Treated Dendritic Cells Modulate Immune Responses of Naïve and Sensitized T Cells in Vivo," pp. 836-841 (2002).

Nishida et al., "Gab-Family Adapter Proteins Act Downstream of Cytokine and Growth Factor Receptors and T—and B-Cell Antigen Receptors," *Blood*, vol. 93, No. 6, pp. 1809-1816 (1999).

Obeid et al., "Calreticulin Exposure Dictates the Immunogenicity of Cancer Cell Death," *Nature Medicine*, vol. 13, No. 1, pp. 54-61 2007).

Raz et al., "B-cell function in new-onset type 1 diabetes and immunomodulation with a heat-shock protein peptide (DiaPep277): a randomized, double-blind, phase ii trial," *The Lancet*, vol. 358, pp. 1749-1753 (2001).

Rogers et al., "Qualitative Changes Accompany Memory T Cell Generation: Faster, More Effective Responses at Lower Doses of Antigen," *The American Assoc. of Immunologists*, vol. 164, pp. 2338-2346 (2000).

Rutella et al., "Tolerogenic Dendritic Cells: Cytokine Modulation Comes of Age," *Blood*, vol. 108, No. 5, pp. 1435-1440 (2006).

Sauter et al., "Consequences of Cell Death: Exposure to Necrotic Tumor Cells, but Not Primary Tissue Cells or Apoptotic Cells, Induces the Maturation of Immunostimulatory Dendtritic Cells," *J. Exp. Med.*, pp. 423-433 (2000).

Sprent et al., "T Cell Memory," *Annu. Rev. Immunol.*, vol. 20, pp. 551-579 (2002).

Steinman et al., "How to Successfully Apply Animal Studies in Experimental Allergic Encephalomyelitis to Research on Multiple Sclerosis," *American Neurological Assoc.*, pp. 12-21 (2006).

Steinman et al., "Tolerogenic Dendritic Cells," *Annu. Rev. Immunol.*, vol. 21, pp. 685-711 (2003).

Steinman, "Immune Therapy for Autoimmune Diseases," *Science*, vol. 305, pp. 212-216 (2004).

Sun et al., "Regulatory T cells in experimental allergic encephalomyelitis. I. Frequency and specificity analysis in normal and immune rats of a T cell subset that inhibits disease," *Intern. Immun.*, vol. 11, No. 3, pp. 307-315 (1998).

Terness et al., "Regulation of human auto- and alloreactive T cells by indoleamine 2,3-dioxygenase (IDO)-producing dendritic cells: too much ado about IDO?," *Blood*, pp. 2480-2486 (2005).

Varela et al., "Tuning inflammation with anti-inflammatory neuropeptides," *Expert Opin. Biol. Ther.*, vol. 7, No. 4, pp. 461-478 (2007).

Vollmer et al., "Clinical trail of a MBP encoding DNA plasmid (BHT-3009) alone or combined with atorvastatin for treatment of multiple sclerosis," S13, p. 65 (2011).

Warren et al., "Intravenous synthetic peptide MBP8298 delayed disease progression in an HLA Class II-defined cohort of patients with progressive multiple sclerosis: results of a 24-month double-blind placebo-controlled clinical trial and 5 years of follow-up treatment," *European Journ. of Neurology*, vol. 13, pp. 887-895 (2006).

Warren et al., "Kinetic Profiles of Cerebrospinal fluid anti-MBP in response to intravenous MBP synthetic peptide DENP$_{85}$VVHFFKNIVTP$_{96}$RT in multiple sclerosis patients," *Multiple Sclerosis*, vol. 6, pp. 300-311 (2000).

Weissert et al., "Protective DNA vaccination against organ-specific autoimmunity is highly specific and discriminates between single amino acid substitutions in the peptide autoantigen," *PNAS*, vol. 97, No. 4, pp. 1689-1694 (2000).

Williams et al., "Effector and Memory CTL Differentiation," *Annu. Rev. Immunol.*, vol. 25, pp. 171-192 (2007).

Wraith et al., "T Cell Recognition as the Target for Immune Intervention in Autoimmune Disease," *Cell*, vol. 57, pp. 709-715 (1989).

Xiao et al., "Therapeutic potential of IFN-ɣ-modified dendritic cells in acute and chronic experimental allergic encephalomyelitis," *Intern. Immun.*, vol. 16, No. 1, pp. 13-22 (2003).

Xiao et al., "Tolerogenic Dentritic Cells: The Ins and Outs of Outcome," *J. Immunother*, vol. 29, No. 5, pp. 465-471 (2006).

(56) References Cited

OTHER PUBLICATIONS

Yao et al., "A Novel Human STE20-related Protein Kinase, HGK, That Specifically Activates the c-Jun N-terminal Kinase Signaling Pathway," *The Journ. of Biol. Chem.*, vol. 274, No. 4, pp. 2118-2125 (1999).

Zhang et al., "Mature bone marrow-derived dentritic cells polarize Th2 response and suppress experimental autoimmune encephalomyelitis," *Multipel Sclerosis*, vol. 8, pp. 463-468 (2002).

International Preliminary Report on Patentability for related International Patent Application No. PCT/EP2009/058169, dated Jan. 5, 2011.

Ehser et al., "Inhibition of Heart Allograft Rejection with Mitomycin C-treated Donor Dendritic cells," *Transplantation*, vol. 83, No. 3, pp. 347-350 (2007). [Abstract].

Chuang et al., "Suppressive Dendritic Cells as a Tool for Controlling Allograft Rejection in Organ Transplantation: Promises and Difficulties," vol. 69, No. 3, pp. 165-173 (2008). [Abstract].

Liu, et al., "The Endothelial Cells Incubated with the Supernatant of MBP-stimulation PBMC can promote T Cell proliferation," vol. 17, No. 2, pp. 112-114 (2001).

Final Office Action issued in related U.S. Appl. No. 14/536,456, dated Oct. 11, 2018.

Office Action issued in related U.S. Appl. No. 14/536,456, dated Dec. 16, 2019.

Office Action issued in related U.S. Appl. No. 14/536,456, dated Jul. 1, 2020.

Jiga, et al., "Generation of Tolerogenic Dendritic Cells by Treatment with Mitomycin C: Inhibition of Allogeneic T-Cell Response is Mediated by Downregulation of ICAM-1, CD80, and CD86," *Transplantation*, vol. 77, pp. 1761-1773 (Jun. 2004).

\* cited by examiner

A

B

IMMUNOSUPPRESSIVE BLOOD CELLS AND METHODS OF PRODUCING THE SAME

CROSS-REFERENCE TO RELATED APPLICATIONS

This application is a divisional of U.S. patent application Ser. No. 14/536,456, filed Nov. 7, 2014, which is a divisional of U.S. patent application Ser. No. 13/001,729, filed May 25, 2011, which is the National Phase of International Patent Application No. PCT/EP2009058169, filed Jun. 30, 2009, which claims priority from European Patent Application No. 08011780.7, filed Jun. 30, 2008. The contents of these applications are incorporated by reference in their entirety.

The present invention refers to a method of producing immunosuppressive blood cells that can be used for the treatment of autoimmune diseases, in particular multiple sclerosis, organ graft rejection and graft-versus-host disease.

INTRODUCTION

The role of autoantigens and autoreactive lymphocytes in the initiation and maintenance of autoimmune diseases has been controversially discussed (1). Even if self-antigens were not the primordial cause of some autoimmune conditions, they offer a way of directing an immunosuppressive effect to the diseased organ, and therefore constitute a promising alternative to the commonly used broadly-reactive immunosuppressants, in a clinical trial, an immunomodulatory peptide derived from hsp60—one of the known target self antigens—was injected into patients with newly diagnosed type 1 diabetes. Although the study was small, it suggested that the peptide treatment preserved endogenous insulin production (3). Tolerance induction was also attempted by oral administration of self-antigens. This has been tried with myelin in multiple sclerosis (MS), collagen in RA, and insulin in type 1 diabetes. Despite success with the prevention of diseases in animal models, clinical trials attempting to treat an ongoing disease in humans have thus far been unsuccessful (4). What has been learned from animal models and the few clinical studies is that autoantigens must be presented in a non-immunogenic form, usually by altering their structure. A successful example for the fatter strategy is treatment of MS patients with copaxone—a synthetic peptide which mimics the composition of the central nervous component, myelin basic protein (4).

Dendritic cells (DCs) are commonly thought of as strongly stimulatory cells, but DCs can also suppress the immune response (5). Evidently, evolution has developed highly efficient mechanisms for protecting tissues and organs from self-destruction, one of them being mediated by DCs (5). What nature applies for protection from self-attack might be used by man for treatment of autoimmune diseases or graft rejection. Unfortunately, natural suppressive DCs are hard to define phenotypically and therefore difficult to use for therapeutic applications. For example, it has been shown that immature DCs induce tolerance, whereas mature DCs activate immune responses (5). However, a growing body of recent evidence indicates that DC maturation per se is not a distinguishing feature of immunogenicity as opposed to tolerogenicity (6). It is presently believed that the development of an immunogenic or tolerogenic response depends on the net effect of antigen dose, DC lineage and maturational status, DC stimulation by pathogen-derived products, and the cytokine milieu (5, 6). Given the hardly predictable suppressive function of natural DCs, a reasonable alternative for therapeutic purposes would be the in vitro generation of inhibitory DCs. Several methods have been described for designing suppressive DCs (7). A major risk of deliberately generated inhibitory DCs is their potential reversibility to a stimulatory status. Furthermore, their effectiveness may be limited to certain species.

DETAILED DESCRIPTION

Jiga et al., (2007) *Transplantation* 83:347-350 describe the use of Mitomycin C for stable transformation of stimulatory into inhibitory dendritic cells. A single injection of such donor DCs into the recipient prior to heart transplantation suppressed heart allograft rejection in rats (8). However, the use of DC's bears the disadvantage that the generation of DC's and the maturation period may lead to variations in the quality of the DC's, which negatively influences the reproducibility of the approach.

Furthermore, the therapeutic use of dendritic cells is still considered problematic as DCs are strongly immunogenic even when converted into suppressive cells.

Thus, the problem underlying the present invention is to provide means for inducing an immune tolerance without evoking the adverse effects observed with conventional therapies. Surprisingly, the inventors have found out that peripheral blood mononuclear cells (PBMC's) or whole blood treated with mitomycin C (MMC) served as powerful tolerance inducers in a rat heart transplantation model.

The strategy for controlling autoimmune reactions envisaged in the present invention is to load MMC-treated human or murine blood cells with self-antigens and to use these "inhibitory bullets" for targeted suppression of specific self-reactive T cells in vitro and in vivo.

Thus, the problem is solved by the present invention, which provides a pharmaceutical composition for treating an inflammatory disease in a patient, said composition comprising isolated immunosuppressive blood cells treated with a therapeutically effective amount of a chemotherapeutic agent, an autoantigen, and optionally a pharmaceutically acceptable carrier.

For the purposes of convenience, "immunosuppressive blood cells" or "blood cells" are hereinafter referred to as "BC's".

As used herein, the term "blood cells" (BC) refers to either whole blood or distinct cell types within the whole blood having the desired properties. These distinct cell types include Peripheral Blood Mononuclear Cells (PBMC) such as a lymphocytes or monocytes, or dendritic cells (DC).

Preferably, the "blood cells" are whole blood or PBMCs. PBMCs can be extracted from whole blood using ficoll, a hydrophilic polysaccharide that separates layers of blood, with monocytes and lymphocytes forming a buffy coat under a layer of plasma. This buffy coat contains the PBMCs. Additionally, PBMC can be extracted from whole blood using a hypotonic lysis which will preferentially lyse red blood cells. This method results in neutrophils and other polymorphonuclear (PMN) cells which are important in innate immune defense to be obtained.

As used herein, the term "chemotherapeutic agent" encompasses any of numerous chemotherapeutic drugs that can be used in the compositions, methods or uses of the invention. These compounds fall into several different categories, including, for example, alkylating agents, antineoplastic antibiotics, antimetabolites, and natural source derivatives.

Examples of alkylating agents that can be used in the invention include busulfan, caroplatin, carmustine, chlorambucil, cisplatin, cyclophosphamide (i.e., cytoxan), dacarbazine, ifosfamide, lomustine, mecholarethamine, melphalan, procarbazine, streptozocin, and thiotepa.

Examples of antineoplastic antibiotics include bleomycin, dactinomycin, daunorubicin, doxoorubicin, idarubicin, mitomycin (e.g., mitomycin C), mitoxantrone, pentostatin, and plicamycin.

Examples of antimetabolites include fluorodeoxyuridine, cladribine, cytarabine, floxuridine, fludarabine, flurouracil (e.g., 5-fluorouracil (5FU)), gemcitabine, hydroxyurea, mercaptopurine, methotrexate, and thioguanine.

Examples of natural source derivatives include mycophenolate (mofetil), docetaxel, etoposide, irinotecan, taxanes (e.g. paclitaxel), teniposide, topotecan, vinblastine, vincristine, vinorelbine, prednisone, and tamoxifen.

Additional examples of chemotherapeutic agents that can be used in the invention include asparaginase and mitotane. Furthermore, also C2 ceramide can be used.

In an especially preferred embodiment, the chemotherapeutic agent is selected from the group consisting of mitomycin C, C2 ceramide, tunicamycin, mycophenoiate-mofetil, tryptophan metabolites (and semisynthetic derivates thereof), and proteasome inhibitors. Tryptophan metabolites are also known as kynurenines, an example of which is Tranilast. Most preferably, the chemotherapeutic agent is mitomycin C.

The person skilled in the art is aware of a variety of antigens or derivatives thereof that can be used in the context of the present invention. These include natural antigens such as MBP (Myelin Basic Protein, human), MOG (Myelin Oligodendrocyte Glycoprotein), PLP (Proteolipid Protein), synthetic peptides such as Copaxone® (also known as copolymer 1 or glatiramer acetate comprising a mixture of randomly synthesized peptides using the following four amino acids: tyrosine, glutamic acid, alanine and lysine; the peptide sequences are based on the naturally occurring human protein MBP) (Teva Pharmaceutical Industries Ltd.), YEAK, VEAK, PEAK (other copolymers based on $MBP_{85-99}$) (Fridkis-Hareli et al., 2002, *J. Clin. Invest.*, 109:1635-1643), natural peptides derived from the above antigens described in Bielekova et al., 2000, *Nature Med.*, 6:1187-1175.), DNA coding for diverse myelin autoantigens, e.g. DNA encoding full length MBP, PLP, MOG, MAG (Ho et at., 2005, *J. Immunol.*, 175:6226-6234), DNA coding for myelin-peptides derived from the proteins MBP, MOG, PLP (Weissert et al., 2000, *PNAS*, 97:1689-1694), antigens from clinical studies such as APL CGP77116 (altered peptide ligand to $MBP_{83-99}$ (Bielekova et al., 2000, *Nature Med.*, 6:1167-1175), APL NBI-5788 (altered peptide ligand to $MBP_{83-99}$ (Kappos et al., 2000, *Nature Med.*, 6:1176-1182), $MBP_{82-96}$ (BioMS Technology Corp., AB. Canada) (Warren et al., 2006, *Eur. J, Neurol.*, 13:887-895. Warren and Catz, 2000, *Multiple Sclerosis*, 6:300-311) and BHT-3009 representing a DNA-construct encoding MBP (Bayhill Therapeutics, Palo Alto, Calif., USA) (Bar-Or et al., 2007, *Arch Neurol.*, 64:1407-1415; Bar-Or et al., 2005, *Multiple Sclerosis*, 11:S167. Vollmer et al., 2005, *Multiple Sclerosis*, 11:S13).

In a preferred embodiment, the antigen used in the context of the present invention is myelin basic protein (MBP). Even more preferred as antigen is a synthetic peptide of MBP, such as Copaxone.

The composition of the present invention is used in the treatment of an inflammatory disease, which is another embodiment of the present invention.

As used herein, the term "treating" or "treatment" as used in relation to the treatment of inflammatory diseases is to be understood as embracing both symptomatic and prophylactic modes, that is the immediate treatment, e.g. of acute inflammation (symptomatic treatment) as well as advance treatment to prevent, ameliorate or restrict long term symptomatology (prophylactic treatment). The term "treatment" as used in the present specification and claims in relation to such diseases is to be interpreted accordingly as including both symptomatic and prophylactic treatment, i.e. symptomatic treatment to ameliorate acute inflammatory events and prophylactic treatment to inhibit ongoing inflammatory status and to ameliorate future bronchial exacerbation associated therewith.

Preferably, "prophylactic treatment" refers to preventing the diseases and disorders referred to in the present application. "Preventing" refers to retaining health with respect to the diseases or disorders referred to herein for a certain period of time in a subject, it will be understood that the said period of time is dependent on the amount of the drug compound which has been administered and individual factors of the subject discussed elsewhere in this specification. It is to be understood that prevention may not be effective in all subjects treated with the compound according to the present invention. However, the term requires that a statistically significant portion of subjects of a cohort or population are effectively prevented from suffering from a disease or disorder referred to herein or its accompanying symptoms. Preferably, a cohort or population of subjects is envisaged in this context which normally, i.e. without preventive measures according to the present invention, would develop a disease or disorder as referred to herein. Alternatively, the prevalence of a disease in a cohort will be significantly reduced with respect to the normal prevalence in a cohort of subjects which have been efficiently prevented (protected) from the disease. Whether a portion is statistically significant can be determined without further ado by the person skilled in the art using various well known statistic evaluation tools discussed below in this specification.

The term "symptomatic treatment" refers to ameliorating the aforementioned diseases or disorders or the symptoms accompanied therewith to a significant extent. In the case of organ graft rejection treatment, preferably, suppresses the rejection so far that the transplanted organ(s) remain(s) functional. Also preferably, graft-versus-host disease is limited by the treatment to such an extent that the patient's organs are not significantly damaged.

It is to be understood that treating as used in accordance with the present invention may not be effective in all subjects to be treated. However, the term shall require that a statistically significant portion of subjects suffering from a disease or disorder referred to herein can be successfully treated. Whether a portion is statistically significant can be determined without further ado by the person skilled in the art using various well known statistic evaluation tools, e.g. determination of confidence intervals, p-value determination, Student's t-test, Mann-Whitney test etc. Preferred confidence intervals are at least 90%, at least 95%, at least 97%, at least 98% or at least 99%. The p-values are, preferably, 0.1, 0.05, 0.01, 0.005, or 0.0001. Preferably, the treatment shall be effective for at least 60%, at least 70%, at least 80%, or at least 90% of the subjects of a given cohort or population.

As used herein, the term "inflammatory disease" refers to diseases which are a result of an individual's immune reaction of connecting tissue and blood vessels to a stimulus, with the purpose to eliminate or inactivate said stimulus. Triggering effectors include mechanical stimuli, or other physical factors, e.g. ionizing radiation, UV light, heat, coldness; chemical substances, e.g. bases, acids, heavy metals, bacterial toxins, allergens, and immune complexes, as well as pathogens, e.g. microorganisms and viruses, worms and insects; and pathogenic metabolism products, malfunctioning enzymes, malign tumors.

As used herein, "therapeutically effective amount" means a sufficient amount of said compound to treat a particular disease, at a reasonable benefit/risk ratio. In general, the term "therapeutically effective amount" shall refer to an amount of said compound which is physiologically significant and improves an individual's health. An agent, i.e. said compound, is physiologically significant if its presence results in a change in the physiology of the recipient human. For example, in the treatment of a pathological condition, administration of said compound which relieves or arrests further progress of the condition would be considered both physiologically significant and therapeutically effective.

As indicated supra, the BC's of the present invention are useful in the treatment of inflammatory diseases. Such inflammatory diseases can be subdivided into chronic inflammatory diseases, acute inflammatory diseases, allergic inflammatory disorders, graft-versus-host rejection diseases, and autoimmune disorders, all of which are encompassed within the present invention. Among these subgroups, inflammatory diseases of the respiratory tract, inflammatory skin diseases, allergic inflammatory disorders, inflammatory diseases of the gastrointestinal tract and inflammatory heart diseases can occur.

Preferably, the BC's of the present invention are useful in the treatment of autoimmune disorders as listed hereinafter.

BC's may also be used to treat any disease or condition of the airways or lung requiring immunosuppressive therapy, e.g., for the treatment of autoimmune diseases of, or as they affect, the lungs (for example, for the treatment of sarcoidosis, alveolitis or chronic hypersensitivity pneumonitis) or for the maintainance of allogenic lung transplant, e.g., following lung or heart lung transplantation.

In a further preferred embodiment of the present invention relates to a pharmaceutical composition for the treatment of organ graft rejection and/or graft-versus-host disease comprising isolated immunosuppressive blood cells treated with a therapeutically effective amount of a chemotherapeutic agent and optionally a pharmaceutical acceptable carrier.

As immunosuppressants, BC's are useful when administered for the prevention of immune-mediated tissue or organ graft rejection. Examples of transplanted tissues and organs which suffer from these effects are heart, kidney, liver, medulla ossium, skin, cornea, lung, pancreas, intestinum tenue, limb, muscle, nervus, duodenum, small-bowel, pancreatic-islet-cell, and the like; as well as graft-versus-host diseases brought about by medulla ossium transplantation.

A preferred embodiment of the present invention relates to the pharmaceutical composition of the present invention for the symptomatic treatment of organ graft rejection and graft-versus-host disease. Preferably, treatment of the rejection of the following organs and tissues is encompassed by the present invention: heart, kidney, liver, medulla ossium, skin, cornea, lung, pancreas, intestinum tenue, limb, muscle, nervus, duodenum, small-bowel and pancreatic-islet-cell. Graft-versus-host disease is, typically, brought about by medulla ossium transplantation. Preferably, the pharmaceutical composition comprises BCs of the donor or the recipient. More preferably, in the case of graft-versus-host disease the BCs are taken from the recipient of the transplant while in the case of organ graft rejection the cells are taken from the donor.

Interestingly, it has been found in the study underlying the present invention that the pharmaceutical composition disclosed in this application cannot only be used for the prophylactic treatment of an organ graft rejection but also for its symptomatic treatment. The mechanisms that are required for the prophylactic treatment of organ graft rejection and for the symptomatic treatment thereof differ considerably. Prophylactic treatment only requires the suppression of relatively few and inactive immune cells, in the naïve unstimulated state a frequency of about one precursor clone in 100,000 CD8+ T cells had been estimated to exhibit specificity for a defined antigen (Blattmann et al., 2002, *J. Exp. Med.*, 195:657-664).

In an acute organ graft rejection the immune cell clones which recognize tissue of the donor have already expanded. Regarding viral infections, within 7-8 days a massive increase in number of specific T-cell clones occurs, up to 50,000-fold comprising about 15 to 20 proliferation cycles (Williams & Sevan, 2007, *Ann. Rev. Immunol.*, 25:171-192). Thus, the activity of a large number of cells has to be suppressed successfully. Moreover active immune cells are in a different physiological state as compared to resting immune cells. In order to initiate proliferation and various effector functions naïve CD4+ and CD8+ T cells need to encounter antigens in lymphoid organs presented by antigen-presenting cells (APCs). Sn contrast activated and expanded T cells swarm to the peripheral tissues to find and subsequently eliminate the antigenic sources. During this extremely complex procedure the activated cells express a mixture of various signaling and effector molecules such as cytokines and chemokines that exhibit uncounted functions upon immune as well as non-immune cells. The exposure to foreign antigens usually results in the appearance of long-lived so-called memory cells making up 5%-10% of the original number of activated effector cells. The quality of the memory cells is reflected by a faster and more effective response to further encounters with the same antigens (Harty & Badovinac, 2008, *Nat. Rev. Immunol.*, 8:107-119; Williams & Bevan, 2007, *Ann. Rev. Immunol.*, 25:171-192; Sprent & Surh, 2002, *Ann. Rev. Immunol.*, 20:551-579; Rogers et al., 2000. *J. Immunol.*, 164:2338-2346. Therefore, the efficacy of the pharmaceutical composition of the present invention for the symptomatic treatment of an organ graft rejection was surprising.

Preferably, the blood cells in the pharmaceutical composition for the symptomatic treatment of organ graft rejection and graft-versus-host disease are peripheral blood mononuclear cells.

The regulation of the immune response by BC's would particularly find utility in the treatment of autoimmune disorders, such as rheumatoid arthritis, systemic lupus erythematous, hyperimmunoglobulin E, Hashimoto's thyroiditis, multiple sclerosis, progressive systemic sclerosis, myasthenia gravis, type I diabetes, uveitis, allergic encephalomyelitis, glomerulonephritis, and the like; and further infectious diseases caused by pathogenic microorganisms, such as HIV. In the particular cases of HIV-1, HIV-2 and related retroviral strains, inhibition of T-cell mitosis would suppress the replication of the virus, since the virus relies upon the host T-cell's proliferative functions to replicate.

In a preferred embodiment, the autoimmune disorder to be treated with the pharmaceutical composition and method of the present invention is multiple sclerosis.

Other treatable conditions would include but are not limited to ischemic bowel diseases, inflammatory bowel diseases, necrotizing enterocolitis, intestinal lesions associated with thermal burns and leukotriene B4-mediated diseases: intestinal inflammations/allergies such as Coeliac diseases, proctitis, eosinophilic gastroenteritis, and mastocytosis; food-related allergic diseases which have symptomatic manifestation remote from the gastrointestinal tract (e.g., migraine, rhinitis and eczema); renal diseases such as interstitial nephritis, Goodpasture's syndrome, hemolytic-uremic syndrome and diabetic nephropathy; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergy sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fasclitis; periodontal disease such as lesions of gingiva, periodontium, alveolar bone and substantia ossea dentis; nephrotic syndrome such as glomerulonephritis; male pattern aleopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infraction): intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drag (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis such as erythema multiforme, linear IgA ballous dermatitis and cement dermatitis: and others such as gingivitis, periodontitis, sepsis, pancreatitis, diseases caused by environmental pollution (for example, air pollution), aging, carcinogenis, metastasis of carcinoma and hypobaropathy; disease caused by histamine or leukotriene-C4 release; Behcet's disease such as intestinal-, vasculo- or neuro-Behcet's disease, and also Behcet's which affects the oral cavity, skin, eye, vulva, articulation, epididymis, lung, kidney and so on.

In this context, the present invention further refers to the use of a composition of the present invention for the manufacture of a medicament for the treatment of an autoimmune disease. The medicament, i.e. the blood cells treated as described above, maybe modified with methods and compounds known to the skilled artisan in order to make them easily administrate to the patient. For example, pharmaceutically acceptable carriers may be added as well.

For example, aqueous liquid compositions of the present invention may be particularly useful for the treatment and prevention of various diseases of the eye such as autoimmune diseases (including, for example, conical cornea, keratitis, dysophia epithelialis corneae, leukoma, Mooren's ulcer, sclevitis and Graves' ophthalmopathy) and rejection of corneal transplantation. In particular, compositions pertaining to the present invention are useful for treating a subject for immune-mediated organ or tissue allograft rejection, a graft-versus-host disease, an autoimmune disease, an obstructive airway disease, a hyperproliferative disease, or an ischemic or inflammatory intestinal or bowel disease.

The specific therapeutically-effective dose level for any particular patient will depend upon a variety of factors including the disorder being treated and the severity of the disorder; the age, body weight, general health, sex and diet of the patient; the time of administration, route of administration, the duration of the treatment; drugs used in combination or coincidental with BC's.

As used herein, the term "pharmaceutically acceptable carrier" means a non-toxic, inert solid, semi-solid or liquid filler, diluent, encapsulating material or formulation auxiliary of any type. Some examples of materials which can serve as pharmaceuticaliy acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes: oils such as peanut oil, cottonseed oil, safflower oil, sesame oil, olive oil, corn oil and soybean oil; glycols, such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, phosphate buffer solutions; non-toxic, compatible lubricants such as sodium lauryl sulfate and magnesium stearate; as well as coloring agents, releasing agents, coating agents, sweetening, flavoring and perfuming agents. Preservatives and antioxidants can also be present in the composition, according to the judgment of the formulator.

The compositions may be administered to humans and other animals orally, rectally, parenterally, intracisternally, intravaginally, intraperitoneally, bucally, or as an oral or nasal spray. The term "parenteral" as used herein refers to modes of administration which include intravenous, intramuscular, intraperitoneal, intrasternal, subcutaneous and intraarticular injection and infusion. Preferably, the administration occurs intravenously, intramuscularly or subcutaneously.

Pharmaceutical compositions of this invention for parenteral injection comprise pharmaceutically-acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

In another aspect, the present invention also provides a method of producing immunosuppressive blood cells, comprising exposing an isolated blood cell sample to a chemotherapeutic agent and/or an autoantigen or a derivative thereof.

Preferably, the BC's are treated first with the autoantigen, and, subsequently with the chemotherapeutic agent, in a manner as described in the example section. However, the person skilled in the art will be able to easily adjust the incubation times and amounts of antigen or chemotherapeutic agent in order to obtain the desired immunosuppressive blood cells.

In some cases, it is desirable to add only the chemotherapeutic agent alone. This is the case, when e.g. donor whole blood or PBMC's are used as immunosuppressive cells for inhibiting transplant rejections. Particularly preferred for this application are tryptophan metabolites (kynurenines). Also preferred for this application is mitomycin C.

The invention also provides a method for treating a patient suffering from an autoimmune disease, said method comprising: a) obtaining a blood cell sample; b) treating said blood cell sample with a chemotherapeutic agent and an autoantigen; and c) administering such treated blood cells to said patient; wherein said treated blood cells ameliorate said autoimmune disease in said patient.

In accordance with this aspect of the invention, blood cells are first loaded or pulsed with one or more antigens, such as one or more autoantigens, and then modified ex vivo with an chemotherapeutic agent as described below in the Example section. In one embodiment, the blood cells are pulsed with one or more diabetogenic autoantigens such as GAD, an islet cell autoantigen (SCA), or autoantigen NRP-A7. In one particular embodiment, blood cells are pulsed with each of GAD 65, ICA 512 and NRP-A7. Alternatively, blood cells may be pulsed with pancreatic islet lysates. In another embodiment, blood cells are pulsed with collagen (for example, to treat arthritis). In another embodiment, blood cells are pulsed with myelin basic protein (MBP) (for example, to treat multiple sclerosis), or a derivative thereof, as described supra.

In a preferred embodiment, the blood cells are pulsed with MBP or a derivative, synthetic peptide thereof, and the autoimmune disease is multiple sclerosis.

In yet another preferred embodiment of the present invention the blood sample is first treated with the autoantigen and subsequently with the chemotherapeutic agent.

In another aspect, the present invention refers to a method for treating a graft recipient, said method comprising a) obtaining a blood cell sample from a donor, b) treating said blood cell sample with a chemotherapeutic agent, and c) administering such treated blood cells to said graft recipient, wherein said treated donor blood cells ameliorate the risk of developing graft rejection in said patient.

Furthermore, the present invention relates to a method for treating a graft recipient, said method comprising
a) obtaining a blood cell sample from a donor, wherein the recipient is suffering from organ graft rejection;
b) treating said blood cell sample with a chemotherapeutic agent; and
c) administering such treated blood cells to said graft recipient, wherein said treated donor blood cells ameliorate the ongoing organ graft rejection in said patient.

In a preferred embodiment, the chernotherapeutic agent is a tryptophan metabolite, most preferably a kynurenine derivative, such as Tranilast. Also preferably, the chemotherapeutic agent is mitomycin C.

In another aspect, the present invention refers to a method for treating a graft recipient, said method comprising
a) obtaining a blood cell sample from a recipient
b) treating said blood cell sample with a chemotherapeutic agent, and
c) administering such treated blood cells to said graft recipient, wherein said treated recipient blood cells ameliorate the risk of developing graft-versus-host disease initiated in said patient.

Furthermore, the present invention relates to a method for treating a graft recipient, said method comprising
a) obtaining a blood cell sample from a recipient, wherein the recipient is suffering from graft-versus-host disease;
b) treating said blood cell sample with a chemotherapeutic agent; and
c) administering such treated blood cells to said graft recipient, wherein said treated recipient blood cells ameliorate the ongoing graft-versus-host disease in said patient.

In a preferred embodiment, the chemotherapeutic agent is a tryptophan metabolite, most preferably a kynurenine derivative, such as Tranilast. Also preferably, the chemotherapeutic agent is mitomycin C.

Figures 1A, 1B, 1C, 1D:
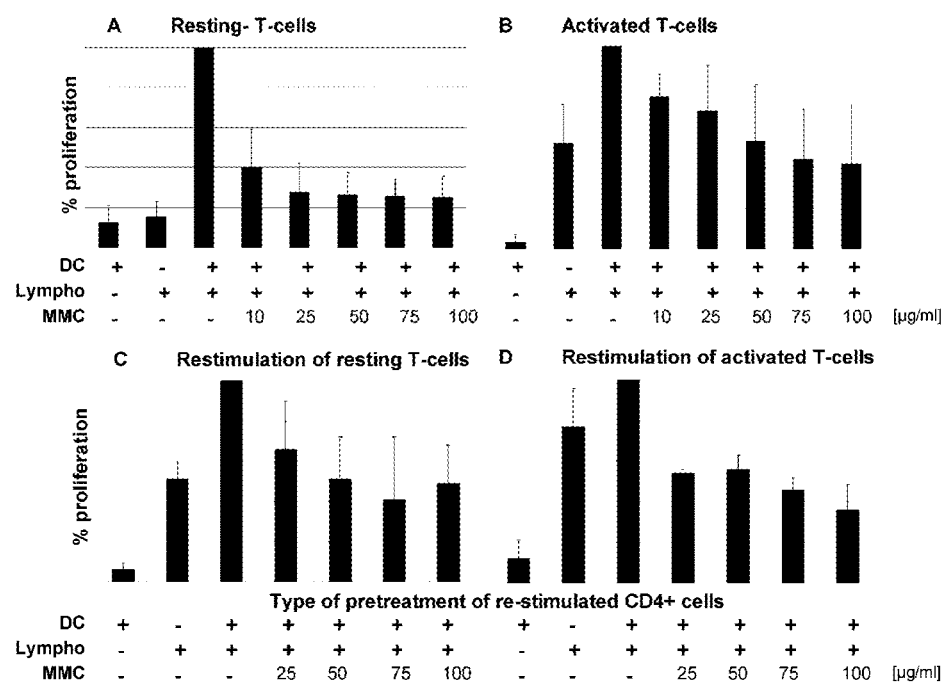
FIGS. 1A-1D. Effect of MMC-treated BCs loaded with MBP on resting or activated T cells from MS patients. Primary stimulation (A, B): MBP-MMC-BCs are co-incubated with resting (A) (n=8) or activated peripheral lymphocytes (B) (n=7). Negative controls: MBP-BCs or lymphocytes only; positive controls: MMC-untreated MBP-BCs plus lymphocytes. Restimulation (C, D): CD4+ cells are isolated and re-stimulated with MBP-BCs of the same donor. Abscissa shows CD4 cells pretreatment. Ordinate shows T-cell proliferation. The first column represents BCs only (negative control). Data represent mean±SD and are expressed as percentage of positive control values (MBP-loaded BCs+lymphocytes=100%).

The invention is further explained by the following examples without being bound to it by any theory.

EXAMPLES

Examples 1

Experimental Procedures (a) Mice

B10.PL mice were obtained from Jackson Laboratories (Bar Harbor, Me.). TCR-transgenic Tg4 mice ($I-Au^u$ background) express a TCR derived from an encephalitogenic CD4+ T cell clone specific for a MBP peptide (aa 1-9)(9).

(b) Generation of Dendritic Cells

Murine DCs are generated from bone marrow cells of B10.PL mice according to the protocol of Lutz et al. (10). For activation, 0.5 μM CpG-ODN 1668 is added. 90 min later non-adherent BMDC's are obtained. WMC (50 μg/ml) is added for 30 min of culture and the cells ($10^6$/ml) are extensively washed. N-terminal acetylated $MBP_{1-10}$ peptide Ac-ASQKRPSQRS (Ac1-10) is added at a concentration of 5 μM in combination with CpG-ODN. Human DCs are generated according to a standard protocol as previously described (11). For MBP-specific T cell studies, 30 μg/ml MSP (Sigma-Aldrich) is added to immature DCs until maturation. MMC (10-100 μg/ml) is added to the DC culture medium; after 30 min of incubation the cells are washed.

(c) T-Cell Studies In Vitro

Murine lymphocytes are cultured with BM-derived BCs. Human peripheral blood lymphocytes of MS patients are co-incubated with autologous MBP-loaded BCs. In a parallel experiment, DRB1*0301-BCs from healthy donors are loaded with MSP and co-incubated with MBP-specific $CD4^+$ T cells (clone ES-BP8T) as previously described (11). In a control experiment, the BCs are loaded with an irrelevant peptide with comparable interaction with DRB1*0301. The HLA restriction can be calculated by the SYFPEITHI software (www.uni-tuebingen.de/uni/kxi). Co-cultures are performed at a BC:T cell ratio of 1:10. T cell proliferation is measured by [$^3$H]thymidine incorporation.

(d) Supernatants of MMC-BCs

Mature BCs are treated with 25, 50 or 75 μg/ml MMC and washed. After 72 h of additional incubation the supernatants are collected and used as cell culture medium in a T-cell proliferation assay. $2 \times 10^5$ cells/well are stimulated for 4 days with anti-CD3 monoclonal antibody (dilution 1:6400).

(e) Cell Cycle Analysis

Lymphocytes are stimulated for 2 days with anti-CD3 monoclonal antibody and cell cycle analysis is performed using the BrdU Flow Kit (BD Pharmingen, Heidelberg, Germany). Cells ($10^6$) are incubated overnight with 10 μM BrdU. After fixation, permeabilization and treatment with 300 μg/ml DNase, the cells are stained with FITC-labeled anti-BrdU antibody and 7-AAD and analyzed by flow cytometry (f) EAE Model EAE is induced by i.v. Injection of $5 \times 10^6$ activated BCs (in 0.2 ml) pulsed with 5 μM of autoantigenic MBP peptide (+/−MMC). On day 1 and 2 after immunization, each mouse is injected i.p. with 200 ng pertussis toxin (Calbiochem, Darmstadt, Germany) in 500 μl DPBS. Symptoms are evaluated daily according to the Coligan score.

(g) Affymetrix Microarray

RNA is converted into ds-cDNA using $T7-(dT)_{24}$ primers and the Superscript Choice system (invitrogen, Karlsruhe, Germany). Biotin-labeled cRNA is generated from the cDNA sample, hybridized to U133 Plus 2.0 gene chips (Affymetrix, High Wycombe, UK), stained with streptavidin-phycoerythrin (MoBiTec, Göttingen Germany) and scanned using the GeneArray scanner (Affymetrix). Microarray data of samples derived from 3 unrelated BC donors are analyzed using the Affymetrix Data Mining tool (DMT 4.0), the Affymetrix publishing tool (MDB 3.0), and the statistical data analysis software (Affymetrix Microarray Suite 5.0). Comparisons between MMC-treated and untreated BCs are done for genes with a positive detection call in at least one experimental group and with a fold change of at least 3 (corresponding to a signal log ratio between the two experimental groups of less than −1.5 or more than 1.5). Functional classifications from Gene Ontology (GO) Consortium (http://www.geneontology.org) are assigned to each identified gene.

(h) FACS Analysis

Human BCs are stained with fluorescein isothiocyanate (FITC)-labefed annexin V and 7-amino-actinomycin (7-AAD) to confirm apoptotic cell death.

BC staining is performed with fluorescence (FITC, PE)-labeled monoclonal antibodies (to MHC II, CD80, CD86,) to concentrations indicated by the manufacturers (BD Biosciences).

(i) Approval for Animal and Human Studies

Animal experiments are approved by the Animal Welfare Board of the Governmental Office Karlsruhe. Studies of human sera and cells are approved by the University of Heidelberg Ethics Committee (k) Statistics Results are shown as mean±SD or SEM as indicated. Single values of T cell proliferation represent the mean [$^3$H]thymidine incorporation (cpm) of triplicate cultures and are given in percentage of the positive control (=100% proliferation) or cpm. P values are calculated by the unpaired Student's t-test using SigmaStat software (SPSS). Statistical significance is set at p<0.05.

Example 2

Results

Myelin-specific T cells have been proposed to play a role in the pathogenesis of MS (1,4). Therefore, MBP represents a candidate antigen for specific immunotherapy in MS. In the following experiments we studied the capacity of MMC-BCs loaded with MBP to control the activity of specific T cells derived from MS patients in cell cultures, and we tested their action in a mouse EAE model.

(a) Myelin-Basic-Protein-Loaded MMC-BCs Inhibit Specific T Cells of Multiple Sclerosis Patients In Vitro BCs derived from MS patients are loaded with MBP and co-incubated with autologous T cells. In a parallel experiment, the BCs are loaded with MBP and treated with MMC. Whereas untreated BCs induce strong T cell stimulation, MMC-BCs do not (FIG. 1A).

Therapy of patients with active MS should address already activated autoreactive T cells. In order to find out whether these lymphocytes can be controlled by inhibitory BCs, pre-activated MBP-specific T cells derived from a MS patient are incubated with HLA-DR-matched, MBP-loaded MMC-BCs. The response of these T cells was significantly reduced (FIG. 1B).

In the next experiment we investigated whether suppressed T cells can be restimulated with naïve MBP-loaded BCs of the same donor. The results show that, once suppressed by MMC-BCs, T cells cannot or can only weakly be re-activated (FIG. 1C, FIG. 1D).

(b) Supernatants of Mitomycin-Treated BCs do not Inhibit the T Cells

Figure 2:
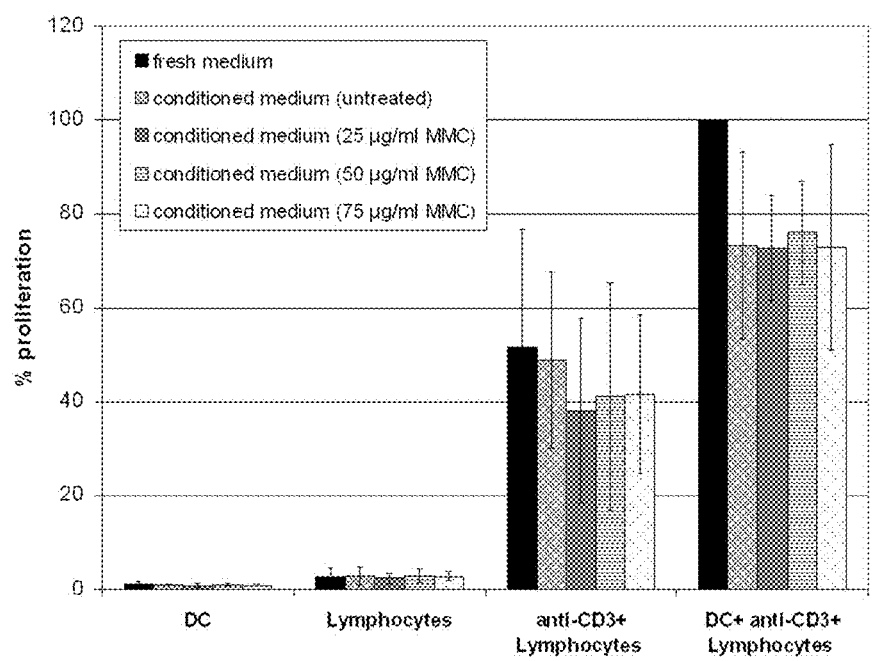
FIG. 2. Influence of MMC-BCs culture medium on stimulated T cells. MMC-treated or untreated BCs are cultivated for 72 h. Supematants (conditioned medium) are collected and used for cultures of anti-CD3 antibody-stimulated T cells with or without autologous BCs. Controls consisted of BCs and lymphocytes only. Data represent mean±SD and are expressed as percentage of positive control values (BC+anti-CD3+lymphocytes=100%) (n=4).

Upon treatment of BCs with MMC a certain amount of substance might have diffused from the intracellular compartment into the culture medium and blocked T cell proliferation, in order to exclude that, supernatants of MMC-treated BCs are collected and used as medium in T cell proliferation assays. The results showed that T cell proliferation is not affected (FIG. 2), indicating that leakage of MMC from treated cells is not the reason for suppression.

(c) T Cells are Blocked in the G0/G1 Phase

When analyzing the mechanism of suppression, two aspects must be considered: the reaction of T cells to inhibitory BCs and the molecular changes of BCs induced by MMC-treatment.

Figures 3A, 3B:
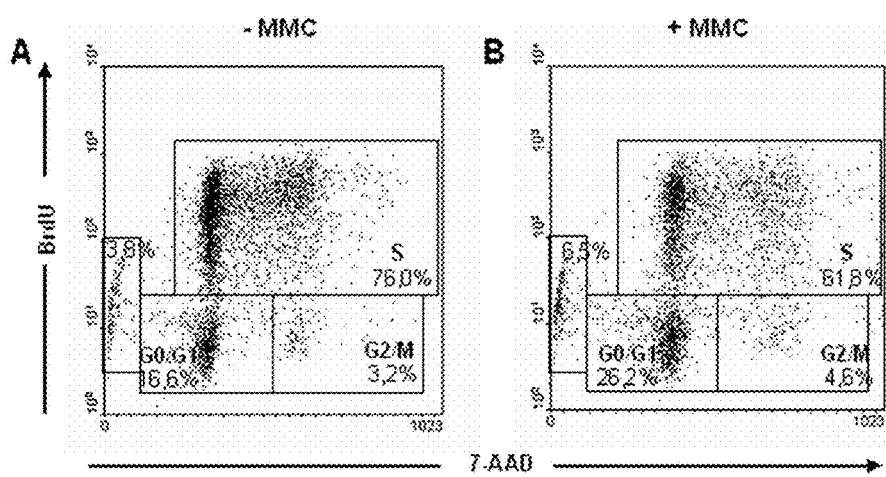
FIGS. 3A-3B. Cell cycle analysis of T celis exposed to MMC-BCs. Anti-CD3 antibody-stimulated T cells are co-cultured with (A) untreated and (B) MMC-treated (25 µg MMC/ml) autologous BCs. Twenty four hrs after supplementation with 10 µM BrdU the cells are analyzed by flow cytometry using a BrdU-Flow-Kit. The displayed quadrants show the percentage of cells in the corresponding cell cycle (G0/G1, G2/M, S) as well as that of dead cells.

As shown in the previous experiment, re-stimulation of suppressed T cells is not or only partially possible, indicating that the cells either became areactive or died. Cell cycle analysis revealed a significant accumulation in the G0/G1 phase of T cells co-incubated with MMC-BCs (FIG. 3). This finding argues for induction of T cell areactivity.

(d) Mitomycin C Does Not Inhibit the Expression of MHC-II and CD80/86 on BC's

MMC might have changed the expression of MHC II or CD80/86. FACS analysis showed that MHC II and CD80/86 are not down-regulated upon incubation with MMC (mean channel of MMC-treated/untreated BCs: MHC II=757/745; CD80=759/728; CD86=751/744); therefore, reduced antigen presentation by lower MHC II density, or less co-stimulation by lower C80/CD86 expression, cannot serve as an explanation for the inhibited T cell proliferation.

Figure 4:
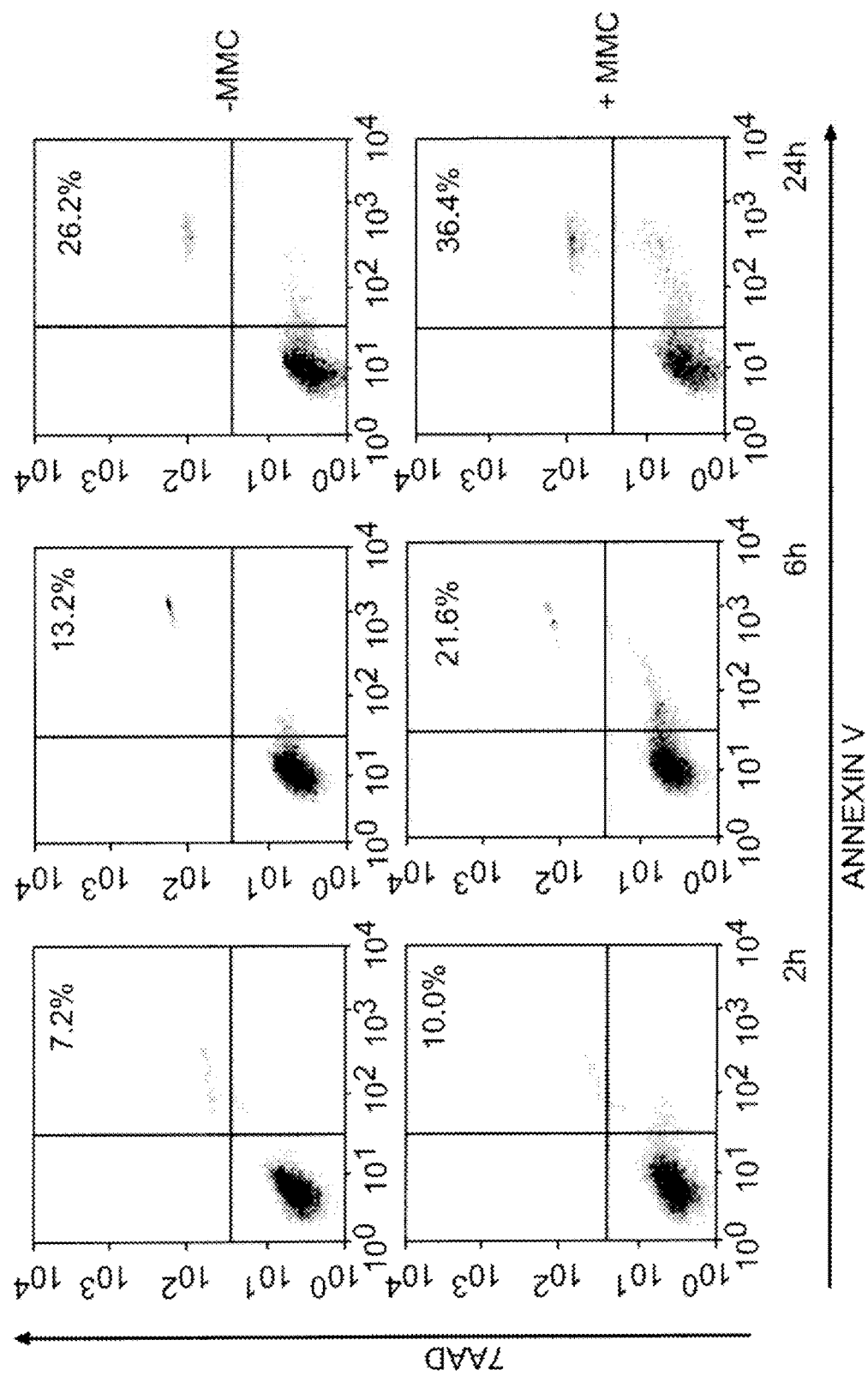
FIG. 4. Flowcytometric analysis of apoptosis following treatment of BCs with MMC. BCs are treated with 50 µg/ml MMC and labelled with annexin-V-FITC and 7-AAD after 2, 6 and 24 hrs of incubation. Controls consisted of untreated BCs (-MMC). The lower and upper right quadrant show apoptosis. Percentages of apoptotic cells are displayed.

(e) Mitomycin C Modulates the Expression of Apoptotic and Immunoregulatory Genes of BC's A comprehensive gene scan of 47,000 transcripts and additional variants was carried out by affymetrix microarray analysis. Genes whose expression was changed more than 3-fold upon treatment of BCs with MMC in 3 independent experiments are further analyzed. Based on this criterion, 116 genes are identified. Among the affected genes, too main clusters are found: one involved in apoptosis and the other mediating immunosuppression. Among apoptosis-related genes, 6 pro-apoptotic genes are upregulated (LRDD, TNFRSF 10b, PERP, FDXR, TRAF4, DDIT3) and 5 anti-apoptotic genes downregulated (NRG2, CFLAR, I-FLICE, Usurpin, FLAME-1), pointing to induction of cell death by apoptosis. It has been speculated that apoptotic cells are tolerogenic (12, 13). Therefore, it was important to verify by FACS whether the changed expression of these genes had repercussions on cell viability. As shown in FIG. 4, MMC-treated BCs enter earlier into apoptosis than untreated BCs. Interestingly, in parallel to apoptotic genes, well known immunosuppressive genes (ADM, TSC22D3, LILRB4) (14-16) are upregulated along with a series of potentially inhibitory genes (MAFB, CSF2RA, MAP4K4, GAB2) (17-21). Taken together, these findings indicate induction of apoptosis and increased expression of immunosuppressive genes in BCs treated with MMC.

(f) Myelin-Basic-Protein-Loaded MMC-BCs Inhibit Specific Mouse T Cells In Vitro

We addressed the question whether the suppressive effect mediated by MMC-BCs in vitro also works in vivo. For clarifying this point, a mouse EAE model is chosen—a setting in which MBP-specific T cells cause an inflammatory disease, similar to the inflammation of MS in humans. A prerequisite for their effectiveness in vivo is that, similarly to human BCs, MMC-treated mouse BCs are T-cell suppressive in vitro. Cell culture studies showed that mouse BCs loaded with MBP and treated with MMC significantly suppress specific syngeneic T cells of Tg4 mice (MBP-MMC-BCs+T cells=12,653±923 vs. MBP-BCs+T cells=24,727±3197; naïve BCs+T cells=7007±1591) (mean of cpm±SEM) (p=0.022).

Previous observations of Liu et al. (13) showed that, when injected into mice, antigen-loaded tolerogenic cells first drive antigen-specific T cells into cell-cycle, and subsequently the T cells are inactivated. This finding prompted us to trace the fate of the deleterious autoreactive T cells in animals treated with inhibitory BCs, MBP-specific T cells are labelled ex vivo with CFSE and injected into syngeneic mice. Thereafter, the animals are injected i.v. with MBP-loaded BCs treated with MMC, and T cells are isolated and analyzed by FACS. The MBP-specific T cells showed a significant degree of proliferation (MBP-MMC-BC=25% vs. MBP-BC=22%). Evidently, in spite of initial stimulation, the T cells must have been subsequently inactivated because, as shown in the following in vivo experiment, they are not able to cause EAE. This finding is in line with the observation described by Liu et al. (13).

Figures 5A, 5B:
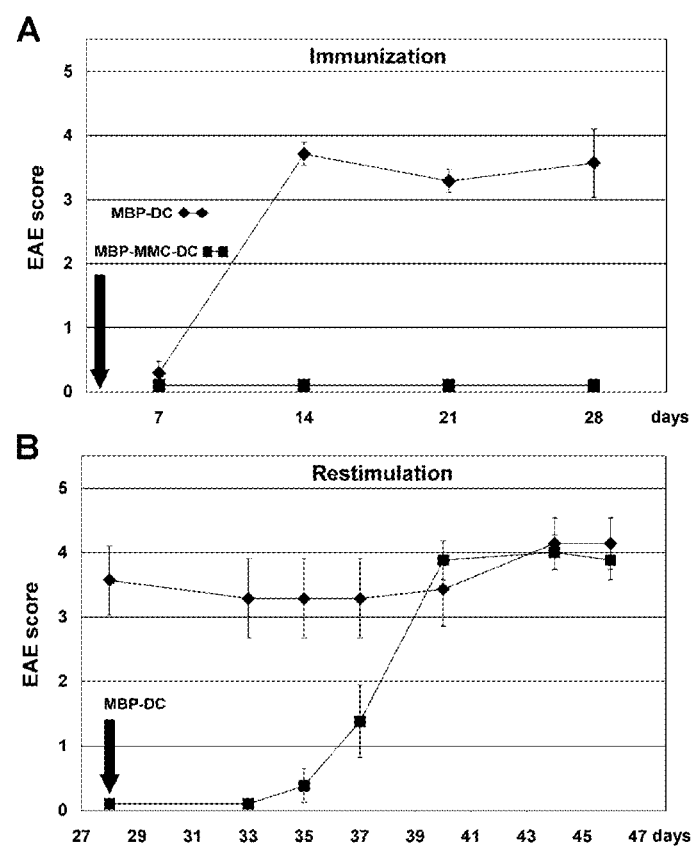
FIGS. 5A-5B. Effect of MMC-treated, MBP-presenting BC's in vivo. (A) Tg4 mice are injected i.v. with either MBP-BCs (♦) or MMC-treated MBP-BCs (■). (B) Mice immunized in experiment A with MMC-treated MBP-BCs (■) are challenged on day 28 with MBP-loaded BCs. Mice immunized in experiment A with MBP-BCs (♦) served as controls. Evaluation of EAE was performed according to the Coligan score. Data are shown as mean values±SEM (n=8 per group).
Figure 6A:
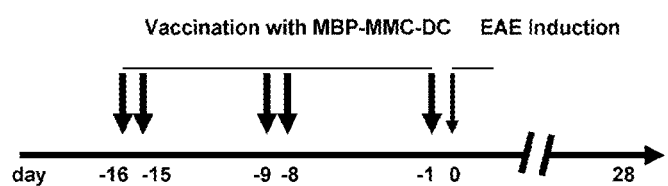
FIGS. 6A-6B. Prophylactic vaccination against EAE with MBP-loaded MMC-treated BC's (A) Tg4 mice are repetitively immunized with MBP-MMC-BCs. On day 0 these (■), as well as non-vaccinated mice (♦), are challenged with MBP-pulsed BCs. (B) The EAE severity (Coligan score) is shown, starting from day 10 after MBP-BC challenge. Data are displayed as mean±SEM (n=8 non-vaccinated, n=10 vaccinated group).
Figure 6B:
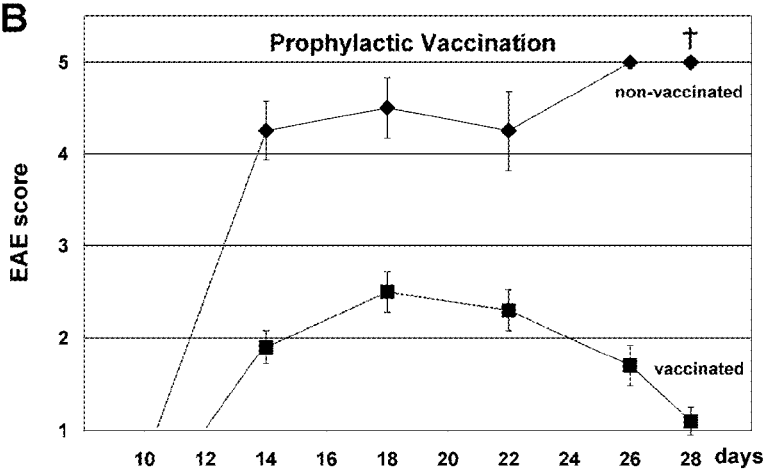
Figure 7:
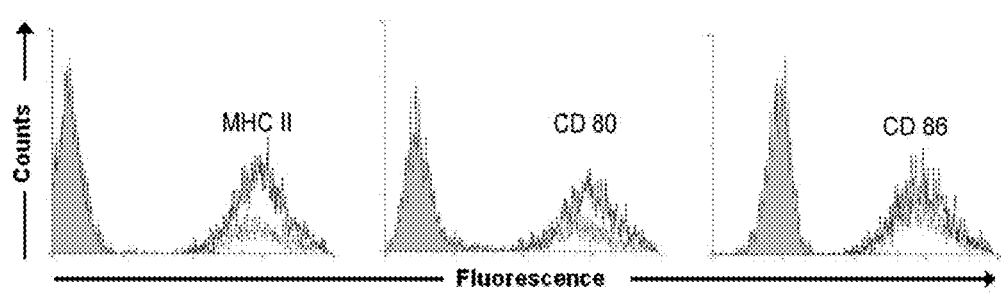
FIG. 7. Phenotype of MMC-treated BCs. MMC-treated (50 μg/ml) and -untreated human BCs are labelled with FITC- or PE-conjugated specific monoclonal antibodies to MHC class II, CD80, CD86, and expression of molecules was analyzed by flow cytometry with a FACScalibur. The binding of antibodies is displayed in the histograms: filled grey histogram represents the isotype control, the red line binding to MMC-treated BCs, and the blue line to MMC-untreated BCs.
Figure 8:
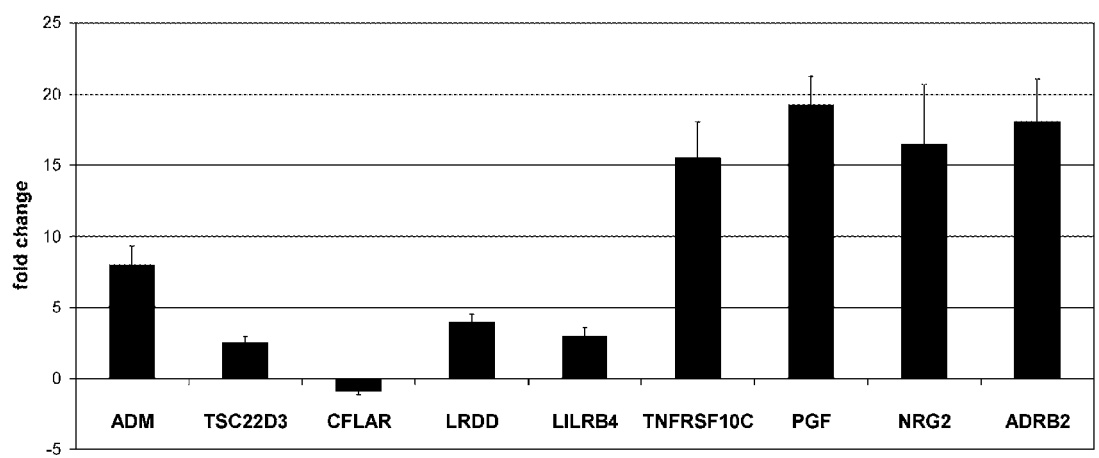
FIG. 8. Quantitative Real Time PCR of MMC-treated dendritic cells. Total RNA of MMC-treated and untreated BCs was extracted 18 hours after treatment, reverse transcribed and analyzed by quantitative real time PCR based on the SYBR green method. Data are normalized to RNA polymerase II. The ordinate shows the fold change of RNA expression levels (±SEM) of MMC-treated BCs as compared to the untreated counterparts (for each gene n≥5)
Figure 9:
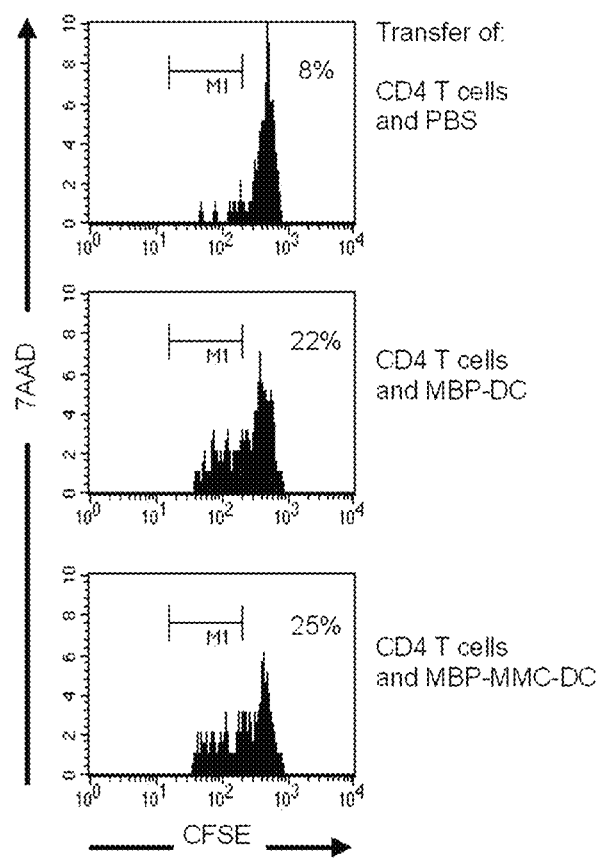
FIG. 9. Effect of MMC-treated blood cells on $CD4^+$-T cells in vivo. MBP-specific TG4 T cells are labelled with CFSE-dye and transferred i.v. to syngeneic B10.PL mice. After 24 h PBS (negative control)(top), MBP-loaded blood cells (positive control)(middle), or MBP-loaded/MMC-treated blood cells (bottom) are injected i.v. After 4 days total lymph node cells are isolated and analyzed for CFSE-staining of $F23.1^+$ (Vβ8.2) $CD4^+$ T cells. Data represent mean percentages of $CFSE^{low}$ proliferating T cells (MBP-MMC-BCs vs. PBS-group: p=0.031; MBP-MMC-BCs vs. MBP-BCs group: p=not significant).

(g) Vaccination with Myelin-Basic-Protein-Loaded MMC-BCs Protects Mice from Experimental Autoimmune Encephalitis MBP-ioaded untreated BCs are injected into animals and, as expected, severe EAE occurs within 2-3 weeks (FIG. 5A). If MBP-loaded BCs are preireated with MMC and then injected, however, the animals remain completely free of symptoms, showing that MBP-specific T cells are not activated. An interesting question is whether the symptom-free animals became resistant to EAE. To this end, treated animals are re-challenged with MBP-BCs. One must keep in mind that the transgenic Tg4 mice used in our study carry >90% MBP-specific T cells, in contrast to only <0.0001% in normal rodents (9, 22). We suspect that it might be difficult to inactivate such a large number of T cells with one injection only. In a subsequent experiment, therefore, the animals are treated 5× with MBP-MMC-BCs and then re-challenged (FIG. 6A). As shown in FIG. 6B, this time the result is positive: whereas controls, which had not been vaccinated with MBP-MMC-BCs, developed severe EAE with lethal outcome, pre-vaccinated mice recovered after a mild episode of disease.

Example 3

Discussion

Attempts to generate regulatory blood cells, in particular dendritic cells (DCs) for control of autoimmune reactions have recently been described. Enk's group generated suppressive DCs by incubating the cells in vitro with IL-10 and inhibited ovalbumin-specific CD4 T-cell responses in naïve and sensitized mice (23). Huang et al. (24) observed that a subpopulation of immature bone marrow-derived DCs, if pulsed with MBP and injected into syngeneic rats, protected from clinical EAE. Others showed that, to the contrary, mature but not immature DCs injected into mice with EAE reduced the severity of clinical signs and inflammation in the CNS (25). These conflicting findings stress the functional plasticity, from immunostimulation to suppression, of DCs under various conditions. Clinical signs of disease could also be reduced if rats or mice with incipient EAE are injected with interferon-γ-treated DCs (26). In neither of the latter two studies are antigen-specific DCs used. By contrast, Menges et al. (27) used tumor-necrosis-factor-α matured DCs pulsed with auto-antigenic peptide and observed protection from EAE if the mice are injected before inductive immunization. Another experimental study suggested that inhibition of NF-κB by pharmacological agents enhanced the capacity of immature DCs to induce antigen-specific suppression to self antigens in mice (28). When murine DCs are transduced with the gene for suppressor of cytokine signaling (SOCS)-3, they exhibited a DC2 phenotype that promoted Th2 cell differentiation and weakly influenced autoimmune reactions in vivo (29). The severity of EAE in mice could also be reduced with autoantigen-loaded DCs expressing TRAIL or PDL1 transgenes (30).

Different functional behaviors of DCs belonging to the same maturational stage (5, 6), the difficulty to standardize the generation of suppressive DCs by biological agents, and reversible modifications induced by cytokines or other biological agents, all are hurdles for the use of suppressive DCs in clinical trials, entailing the risk of stimulating instead of inhibiting the immune response. Ideally, inhibitory DCs for clinical application should be easily and reproducibly generated, stable in their suppressive action, and capable of irreversibly inactivating autoreactive T cells.

Based on our previous experience in rats (8), in which allograft rejection was successfully controlled by MMC-BCs, stably inhibitory DCs for control of autoimmunity are generated in the present study by treating the cells with MMC and loading with autoantigen. These cells protected animals from lethal EAE, showing that, in principle, effective prophylactic vaccination against T cell mediated auto-aggression is possible. MMC is an alkylating agent used in cancer therapy which strongly binds to distinct DNA sites, cross-links the double helical strands, inhibits DNA synthesis, and consequently suppresses cell proliferation. In addition, MMC inhibits RNA and protein synthesis. Interestingly, alkylating agents not only inhibit but also activate pathways usually triggered by stimulatory agents (31). Therefore, it is not surprising that in our model the expression of certain DC-genes was up- and not down-regulated. Because of the irreversible interaction of MMC with intracellular compounds, cells do not release MMC upon incubation with this substance. This was confirmed by our finding that supernatants of MMC-treated DCs do not suppress T cell reactions. Most importantly, in contrast to manipulations of DCs with biological agents (e.g. cytokines), MMC-treatment induces irreversibly suppressive DCs by induction of apoptosis, a feature that offers a potential for developing a stable therapeutic tool. Another advantage of this model is the use of non-toxic doses of a clinically approved drug. The therapeutic dose of MMC is 10-20 mg/m$^2$; the concentration of MMC used in this study for incubation of cells was 0.05-0.100 mg/ml. Our analyses showed that after extensive washing the cell suspension contained, if at all, non-active traces of MMC. No clinical side effects are expected at these minimal amounts of free MMC in the injected solution.

Our findings demonstrate that MMC-BCs are effective in controlling both mouse and human autoreactive T cells. Previous studies in our laboratory showed that MMC-BCs are strongly inhibitory in rats (8). In difference to other models, the therapeutic tool described herein works across species. Moreover, in the present study the in vivo effect was tested under aggravating conditions. Normal rodents carry less than $10^{-6}$ MBP-reactive T cells in their repertoire (22). We used TG4 transgenic mice with >90% MBP-reactive T cells and consequently with an extreme proneness to EAE (9). If this huge number of "dangerous" T cells can be kept in check, we can expect a reliable effect when lower numbers of autoreactive T cells are involved.

Concerning the mechanism of suppression of autoreactive T cells derived from MS patients, we were concerned that MMC-BCs simply might "lose" their stimulatory capacity due to cell death. Our findings, however, show that suppressed T cells cannot be reactivated. Moreover, animals vaccinated with autoantigen-loaded inhibitory DCs became areactive to re-stimulation with the same antigen. These are signs of active suppression instead of a lacking immune response.

A previous study showed that exposure to necrotic tumor cells, in contrast to exposure to apoptotic cells, induces immunostimulation (12). This, as well as other observations (13), led to the hypothesis that necrotic cell death is immunogenic, whereas apoptotic cell death is poorly immunogenic or even tolerogenic. From a physiological standpoint of view this makes sense, because apoptosis is the normal process of cell death in our tissues. Would apoptosis induce immune responses, it would lead to inflammation and autoimmunity. Liu et al. (13) used this phenomenon to actively induce tolerance. Dying apoptotic splenocytes are loaded with ovalbumin and injected into syngeneic mice. After an initial phase of T cell stimulation the recipients became tolerant to ovalbumin (13). It is interesting to note the reports showing that DC lifespan has important consequences for DC-T-cell interaction, and thus determines the immunological outcome. Hugues et al. concluded that stable interactions favor T cell priming, whereas brief contacts between DCs and T cells may contribute to the induction of T cell tolerance (32). In the present series of experiments, MMC accelerated the natural process of apoptosis, shortening the lifespan of injected DCs and thus their contact with T cells. This provides a possible explanation for the observed tolerogenic effect. Obeid et al. (33) has recently analyzed the immunogenic potential of tumor cells rendered apoptotic by various chemotherapeutic drugs and observed that anthracyclins generate stimulatory cells whereas other drugs, such as mitomycin C, do not. If anthracyclins are used, the chaperon protein calreticulin was upregulated and responsible for the stimulatory action. This finding is important for tumor therapy, which aims at killing malignant cells and concomitantly stimulating the immune response against the tumor. Our findings are interesting in this context by demonstrating that treatment with MMC renders the cells apoptotic but—as shown by affymetrix microarray—does not upregulate calreticulin; instead, it upregulates immunosuppressive molecules. Whereas the observation of Obeid et al. (33) may be used for improving chemotherapy in cancer, our observation has a therapeutic potential for controlling autoimmune disease or graft rejection.

In the present study, induction of apoptosis was suggested by upregulation of pro-apoptotic genes, including LRDD (coding for PIDD), TNFRSF10b (coding for TRAIL-R2), PERP, FDXR, TRAF4, and DDIT3. Additionally, we noted downregulation of genes which protect from apoptosis, such as NRG2 and CFLAR (coding for cFLIP and its variants I-FLICE, usurpin, FLAME-1). Most importantly, apoptosis of MMC-treated DCs was demonstrated by FACS.

Gene expression analysis showed that, concomitantly with induction of apoptosis, a series of strongly immunosuppressive genes are upregulated. ADM (adrenomedullin), whose expression was increased 10 times, is a peptide that prevents sepsis-induced mortality, abrogates colitis, and provides highly effective therapy of arthritis by decreasing the presence of autoreactive Th1 cells, inducing regulatory T cells and inhibiting autoimmune and inflammatory responses (14). Another gene whose expression was upregulated by MMC was TSC22D3 (coding for GILZ). Interestingly, the same gene is upregulated upon exposure of DCs to glucocorticoids, IL-10, or TGF-$\beta$, all well-known immunological inhibitors (15). GILZ confers a suppressive phenotype to DCs and prevents them from activating T cells (15). A molecule induced by GILZ is LILRB4 (coding for ILT3), a protein which renders monocytes and DCs tolerogenic and has clinical relevance (16). Human heart transplant recipients with stable grafts have circulating T suppressor cells which upregulate ILT3 in donor antigen-presenting cells (16). These findings demonstrate an important immunoregulatory function of ILT3. We found a significant increase of ILT3expression in MMC-BCs. Other functionally relevant genes whose expression was modulated by MMC are MAFB—which directs differentiation away from DCs towards monocytes (17), CSF2RA—which transduces GM-CSF signals (18), MAP4K4—which mediates TNF-$\alpha$ signalling and cell migration (19, 20), and GAB2—which transmits signals delivered by cytokine-, growth factor-, and antigen-receptors (21). All of them might play a role in immunosuppression induced by MMC-treated DCs.

Taken together, the observations of Obeid et al. (33) and ours suggest that induction of apoptosis with concomitant upregulation of activatory molecules renders cells immunogenic, whereas apoptosis and upregulation of inhibitory molecules renders cells immunosuppressive.

In the 1970s, a random copolymer of amino acids, termed glatiramer acetate, was developed to mimic the composition of MBP. In clinical trials, glatiramer slowed progression of disability and significantly reduced the relapse rate of MS (34). Studies showed that the copolymer tolerized against a variety of different myelin antigens. More recently, altered peptide ligands of MBP and other auto-antigens constructed by substituting amino acids at the contact sites of these epitopes with the T cell receptor showed similar effects in animal models (4). These and other observations (35) indicate that the use of a single epitope can inhibit a disease caused by reactivity to multiple self-epitopes by directing unspecific regulatory mechanisms towards a certain organ. Apparently, in contrast to epitope "spreading", epitope "containment" is also possible. Based on these observations, it is conceivable that MMC-BCs loaded with MBP, although addressing the immune response to one antigen, also can control reactions to neighboring molecules. An elegant variant of our model would be to load the inhibitory DCs with glatiramer acetate or other altered peptides derived from autoantigens. The suppressive action of peptides would be expected to be amplified.

Our in vivo data are derived from studies in the murine EAE model. It has been questioned to which extent this model reflects the pathogenesis of MS in humans (1). Of course, no mouse data, including those derived from EAE studies, can be automatically extrapolated to humans. It is worth mentioning, however, that in spite of all criticism 3 therapeutic compounds approved for use in MS—glatiramer acetate, mitoxantrone and natlizumab—emerged directly from findings in the EAE model (36). Our observations in mice gain additional relevance by the finding that T cells of MS patients are also suppressed by MBP-loaded MMC-BCs.

REFERENCES

1. Hemmer B. Arehelos J-J; Hartung H-P (2002) *Nat Rev Neurosci* 3:291-301.
2. Kamphuis S, Albani S, Prakken B-J (2006) *Expert Opin Biol Ther* 6:579-589.
3. Raz I, Elias D, Avron A, Tamir M, Metzger M. Cohen I-R (2001) *The Lancet* 358:1749-1753.
4. Steinman L (2004) *Science* 305:212-216.
5. Steinman R-M, Hawiger D, Nussenzweig M-C (2003) *Ann Rev Immunol* 21:685-711.
6. Rutella S, Danese S, Leone G (2006) *Blood* 108:1435-1440.
7. Xiao B, Huang Y, Link H (2006) *J immunother* 29:465-471.
8. Jiga L, Ehser S, Kieist C, Opelz G, Terness P (2007) *Transplantation* 83:347-350.
9. Wraith D-C, McDevitt H-O, Steinman L. Acha-Orbea H (1989) *Celt* 57:709-715.
10. Lutz M-B. Kukutsch N, Ogilvie A-L-J, Rossner S, Koch F, Romani N, Schuler G (1999) *J Immunol Methods* 223:77-92.
11. Terness P, Chuang J-J, Bauer T, Jiga L, Opelz G (2005) *Blood* 105:2480-2486.
12. Sauter B, Albert M-L, Francisco L, Larsson M, Somersan S, Bhardwaj N (2000) *J Exp Med* 191:423-434.
13. Liu K, Iyoda T, Saternus M, Kimura Y, Inaba K, Steinman R-M (2002) *J Exp Med* 196:1091-1097.
14. Vareia N, Chorny A, Gonzalez-Rey E, Delgado M (2007) *Expert Opin Biol Ther.* 7:461-78
15. Cohen N, Mouly E, Hamdi H, Maillot M-C, Pallardy M, Godot V, Capel F, Balian A, Naveau S, Galanaud P et al., (2006) *Blood* 107:2037-2044.
16. Chang C-C, Ciubotariu R, Manavalan J-S, Yuan J, Colovai A-I, Piazza F, Lederman S, Colonna M, Cortesini R, Dalla-Favera R et al., (2002) *Nat Immunol* 3:237-243.

17. Bakri Y, Sarrazin S, Mayer U-P, Tillmanns S, Nerlov C, Boned A, Sieweke M-H (2005) *Blood* 105:2707-2716.

18. Crosier K, Wong G, Mathey-Prevot B, Nathan D, Sieff C (1991) *Proc Natl Acad Sci USA* 88:7744-7748.

19. Yao Z, Zhou G, Wang X-S, Brown A, Diener K, Gan H, Tan T-H (1999) *J Biol Chem* 274:2118-2125.

20. Collins C, Hong J, Sapinoso L, Zhou Y, Liu Z, Micklash K, Schultz P, Hampton G (2006) *Proc Natl Acad Sci USA* 103:3775-3780.

21. Nishida K, Yoshida Y, Itoh M, Fukada T, Ohtani T, Shirogane T, Atsumi T, Takahashi-Tezuka M, Ishihara K, Hibi M et al., (1999) *Blood* 93:1809-1816.

22. Sun D, Whitaker J, Wilson D (1999) *Immunol* 11:307-315.

23. Müller G, Müller A, Tüting T, Steinbrink K, Saloga J, Szalma C, Knop J, Enk A-H (2002) *J Invest Dermatol* 119:836-841.

24. Huang Y-M, Yang J-S, Xu L-Y, Link H, Xiao B-G (2000) *Clin Exp Immunol* 122:437-444.

25. Zhang G, Kishi M, Xu H, Rostami A (2002) *Multiple Sclerosis* 8:463-468.

26. Xiao B-G, Wu X-C, Yang J-S, Xu L-Y, Liu X, Huang Y-M, Bjelke B, Link H (2004) *Int Immunol* 16:13-22.

27. Menges M, Rossner S, Voigtlander C, Schindler H, Kukutsch N-A, Bogdan C, Erb K, Schuler G, Lutz M-B 2002 *J Exp Med* 195:15-22.

28. Iruretagoyena M-I, Sepulveda S-E, Lezana J-P, Hermoso M, Bronfman M, Gutierrez M-A, Jacobelli S-H, Kalergis A-M (2006) *J Pharmacol Exp Ther* 318:59-67.

29. Li Y, Chu N, Rostami A, Zhang G-X (2006) *J Immunol* 177:1679-1688.

30. Hirata S, Senju S, Matsuyoshi H, Fukuma D, Uemura Y, Nishimura Y (2005) *J Immunol* 174:1888-1897.

31. Liu Z-G, Baskaran R, Lea-Chou E-T, Wood L-D. Chen Y. Karin M, Wang J-Y-J (1996) *Nature* 384:273-276.

32. Hugues S, Fetler L, Bonifaz L, Helft J, Amblard F, Amigorena S (2004) *Nat Immunol* 5:1235-1242.

33. Obeid M, Tesniere A, Ghiringhelli F, Fimia G-M, Apetoh L, Perfettini J-L, Castedo M, Mignot G, Panaretakis T, Casares N et al., (2007) *Nat Med* 13:54-61.

34. Johnson K, Brooks B, Cohen J, Ford C, Goldstein J, Lisak R, Myers L-W, Panitch H, Rose J, Schiffer R (1995) *Neurology* 45:1268-1276.

35. Lo J, Clare-Salzler M-J (2006) *Autoimmun Rev* 5:419-423.

36. Steinman L. Zamvil S (2006) *Ann Neurol* 60:12-21.

The invention claimed is:

1. A method for treating graft-versus-host disease in a patient, wherein the method comprises:
   (a) obtaining a blood cell sample from the patient and, optionally, preparing Peripheral Blood Mononuclear Cells (PBMCs) from the blood cell sample;
   (b) treating the blood cell sample or PBMCs derived therefrom with mitomycin C; and
   (c) administering the treated blood cells or PBMCs of (b) to the patient;
   wherein the patient is a graft recipient, and wherein administration of the treated blood cells or PBMCs results in T cell suppression, thereby ameliorating the risk of developing graft-versus-host disease in the patient;
   wherein the treated blood cells or PBMCs administered to the patient comprise lymphocytes, monocytes, and dendritic cells.

2. A method for treating autoimmune disease in a patient, wherein the method comprises:
   (a) obtaining a blood cell sample from the patient and, optionally, preparing Peripheral Blood Mononuclear Cells (PBMCs) from the blood cell sample;
   (b) treating the blood cell sample or PBMCs derived therefrom with an autoantigen and with mitomycin C, and
   (c) administering the treated blood cells or PBMCs of (b) to the patient;
   wherein the method results in T cell suppression to treat the autoimmune disease; and
   wherein the treated blood cells or the PBMCs are not enriched or further expanded in culture following treatment with the autoantigen.

3. The method of claim 2, wherein the treated blood cells or PBMCs ameliorate the autoimmune disease in the patient.

4. The method of claim 2, wherein the blood cell sample or PBMCs derived therefrom is first treated with the autoantigen and subsequently with the mitomycin C.

5. The method of claim 2, wherein the blood cell sample or PBMCs derived therefrom is first treated with the mitomycin C and subsequently with the autoantigen.

6. The method of claim 2, wherein the autoantigen is selected from the group consisting of natural antigens, synthetic peptides and natural peptides.

7. The method of claim 2, wherein the autoimmune disease is selected from the group consisting of rheumatoid arthritis, systemic lupus erythematosis, hyperimmunoglobulin E, Hashimoto's thyroiditis, multiple sclerosis, progressive systemic sclerosis, myasthenia gravis, type I diabetes, uveitis, allergic encephalomyelitis, and glomerulonephritis.

8. The method of claim 2, wherein the autoimmune disease is type I diabetes and the autoantigen is a diabetogenic autoantigen.

9. The method of claim 2, wherein the autoimmune disease is multiple sclerosis and the autoantigen is a synthetic peptide of the myelin basic protein, preferably copaxone.

10. The method of claim 1, wherein the patient is a graft recipient, and wherein the method is directed to prophylactically or symptomatically treating graft-versus-host disease in the patient.

11. A method for treating an autoimmune disease, or graft-versus-host disease in a patient, wherein the method comprises suppressing T cells in a patient by administering to the patient a composition comprising:
   (a) isolated blood cells treated with a therapeutically effective amount of mitomycin C, and optionally an autoantigen or a derivative thereof, wherein the isolated blood cells comprise lymphocytes, monocytes, and dendritic cells and are not enriched or further expanded in culture following treating with the autoantigen, wherein the isolated blood cells are isolated from the patient, and
   (b) optionally, a pharmaceutically acceptable carrier.

12. The method of claim 1, wherein the treated blood cells or PBMCs are washed to remove excess mitomycin C prior to administering the treated blood cells or PBMCs of (b) to the patient.

13. The method of claim 11, wherein the autoantigen is selected from the group consisting of natural antigens, synthetic peptides and natural peptides.

14. A method for treating organ graft rejection in a patient, wherein treating does not comprise prophylaxis and wherein the method comprises:
   (a) obtaining a blood cell sample from the patient and, optionally, preparing Peripheral Blood Mononuclear Cells (PBMCs) from the blood cell sample;

(b) treating the blood cell sample or PBMCs derived therefrom with mitomycin C a chemotherapeutic agent; and (c) administering the treated blood cells or PBMCs of (b) to the patient;

wherein the method results in T cell suppression to treat organ graft rejection; and wherein the treated blood cells or PBMCs administered to the patient comprise lymphocytes, monocytes, and dendritic cells.

15. The method of claim 1, wherein the method is directed to prophylactically or symptomatically treating graft-versus-host disease, and wherein the blood cell donor is the graft recipient.

16. The method of claim 14, wherein the method is directed to symptomatically treating organ graft rejection, and wherein the blood cell donor is a graft donor.

17. The method of claim 15, wherein the treated donor blood cells ameliorate the risk of developing graft-versus-host disease in the patient.

18. A method for symptomatic treatment of organ graft rejection in a patient, wherein the method comprises:

(a) obtaining a blood cell sample and, optionally, preparing PBMCs from the blood cell sample;

(b) treating the blood cell sample or PBMCs derived therefrom with mitomycin; and (c) administering the treated blood cells or PBMCs of (b) to the patient;

wherein the method results in T cell suppression to symptomatically treat organ graft rejection, and wherein the treated blood cells or PBMCs administered to the patient comprise lymphocytes, monocytes, and dendritic cells.

\* \* \* \* \*